Figure 1:
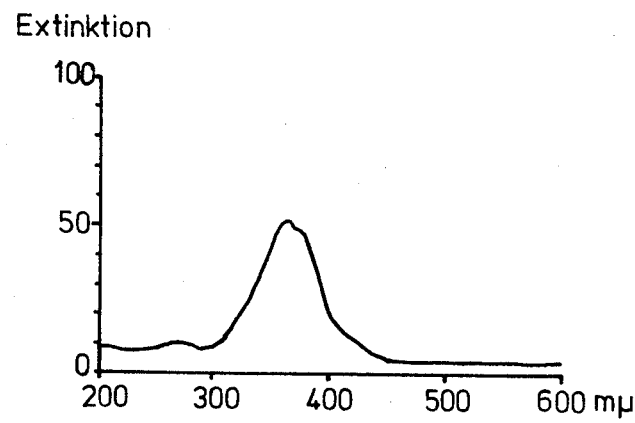

United States Patent [19]

Bauer et al.

[11] 4,264,591

[45] Apr. 28, 1981

[54] ANTIBIOTIC, ITS PRODUCTION AND ITS MEDICINAL USE

[75] Inventors: Klaus Bauer; Wolfgang Gau; Wilfried Kaufmann; Jörg Pfitzner; Martin Scheer; Theo Schröder, all of Wuppertal, Fed. Rep. of Germany

[73] Assignee: Bayer Aktiengesellschaft, Leverkusen, Fed. Rep. of Germany

[21] Appl. No.: 86,114

[22] Filed: Oct. 18, 1979

[30] Foreign Application Priority Data

Oct. 10, 1978 [DE] Fed. Rep. of Germany ....... 2848793

[51] Int. Cl.³ .............................................. A61K 31/71
[52] U.S. Cl. ................................ 424/181; 536/17 R; 435/169
[58] Field of Search .......................... 424/181; 536/17; 435/169

*Primary Examiner*—Jerome D. Goldberg
*Attorney, Agent, or Firm*—Sprung, Felfe, Horn, Lynch & Kramer

[57] ABSTRACT

The invention relates to the provision of an antimicrobial antibiotic obtained by culturing Actinoplanes strain ATCC 31440 under aerobic conditions in the presence of sources of carbon and nitrogen and in the presence of trace amounts of minerals. In addition to their use as antimicrobials, the antibiotics of the invention can be used for improving the growth and feed utilization in animals.

15 Claims, 4 Drawing Figures

ANTIBIOTIC, ITS PRODUCTION AND ITS MEDICINAL USE

The present invention relates to a new antibiotic, a microbiological process for its production from a strain of Actinoplanaceae and its use as an antimicrobial agent in medicine and as an agent for promoting the growth and increasing the feed utilization of animals.

It has already been disclosed that a number of antibiotics of microbial origin possess antimicrobial effects. The spectrum of action of these antibiotics is in part not fully satisfactory. The antibiotics frequently exhibit other disadvantages also. $\beta$-Lactam antibiotics are frequently inactivated by penicillinase. Chloramphenicol, tetracyclins and streptomicin in many cases show considerable undesired side-effects (compare Walter Heilmeyer, Antibiotika-Fibel (Antibiotics Manual), Georg Thieme Verlag, Stuttgart, 3rd edition, 1969, pages 248, 278-280 and 311-319).

It has now been found that a new antibiotic is obtained if the Actinoplanes strain SE 73/34 d (Kl.) is cultured in a nutrient medium and the antibiotic is isolated from the nutrient medium in accordance with known methods.

The above-mentioned strain of Actinoplanes is a spontaneous mutant of the Actinoplanes strain SE 73 (ATCC 31058).

Further, it has been found that the new antibiotic exhibits a powerful antimicrobial effect and furthermore has the property of improving the growth and feed utilisation of animals.

According to the present invention there is provided a compound which is an antibiotic which (a) is a neutral compound and does not migrate on electrophoresis, (b) consists of carbon, hydrogen and oxygen, (c) shows a maximum, in the UV spectrum, at $\lambda = 365$ nm, (d) is readily soluble in chloroform, acetone, ethyl acetate, acetonitrile, dimethylformamide, dimethyl sulphoxide, methanol and ethanol, and sparingly soluble in water, diethyl ether, petroleum ether and cyclohexane, (e) contains methoxy groups and (f) on hydrolysis with 10% strength by weight sulphuric acid at 80° C. splits off reducing sugars. The antibiotic according to the present invention is alternatively characterised in that it possess UV, IR and NMR spectra essentially as shown in FIGS. 1 to 4. The present invention provides such an antibiotic which possess the empirical overall formula $$C_{73}H_{110}O_{37}$$

calculated from the elementary analysis.

The compound according to the invention is characterised in more detail by the following chemical and physical properties:

(1) Elementary analysis and empirical formula

| Calculated for | C 73 | H 110 | O 37 | (1578.6) |
|---|---|---|---|---|
| Calculated: | C 55.5 | H 7.0 | O 37.5 | $40CH_3 = 7.9$ |
| Found+: | C 55.6 | H 6.9 | O 37.8* | $OCH_3 = 7.9$ |

+After drying for 4 days in a high vacuum at 100° C.
*Calculated by difference

It must be pointed out that with such large molecules the limits of error of the elementary analysis do not permit the calculation of a precise empirical formula (R. B. Woodward, Angew, Chem. 69, 50-51 (1957)). The complete empirical formula can therefore exhibit a certain error.

(2) Melting point: 164°-172° C. (with decomposition)

(3) Ultraviolet absorption spectrum:

The UV spectrum of the antibiotic is shown in FIG. 1 (abscissa: wavelength in $\mu$m, and ordinate: extinction)

$\lambda_{max} = 365$ nm (C=0.64 mg in 50 ml of methanol)

$$[E \frac{1\%}{cm}] \, 365 \text{ nm} = 406$$

Figure 2:
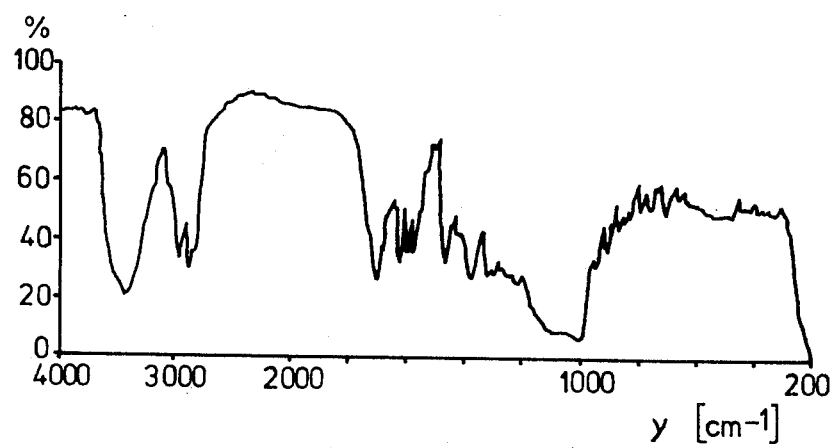
Figure 3:
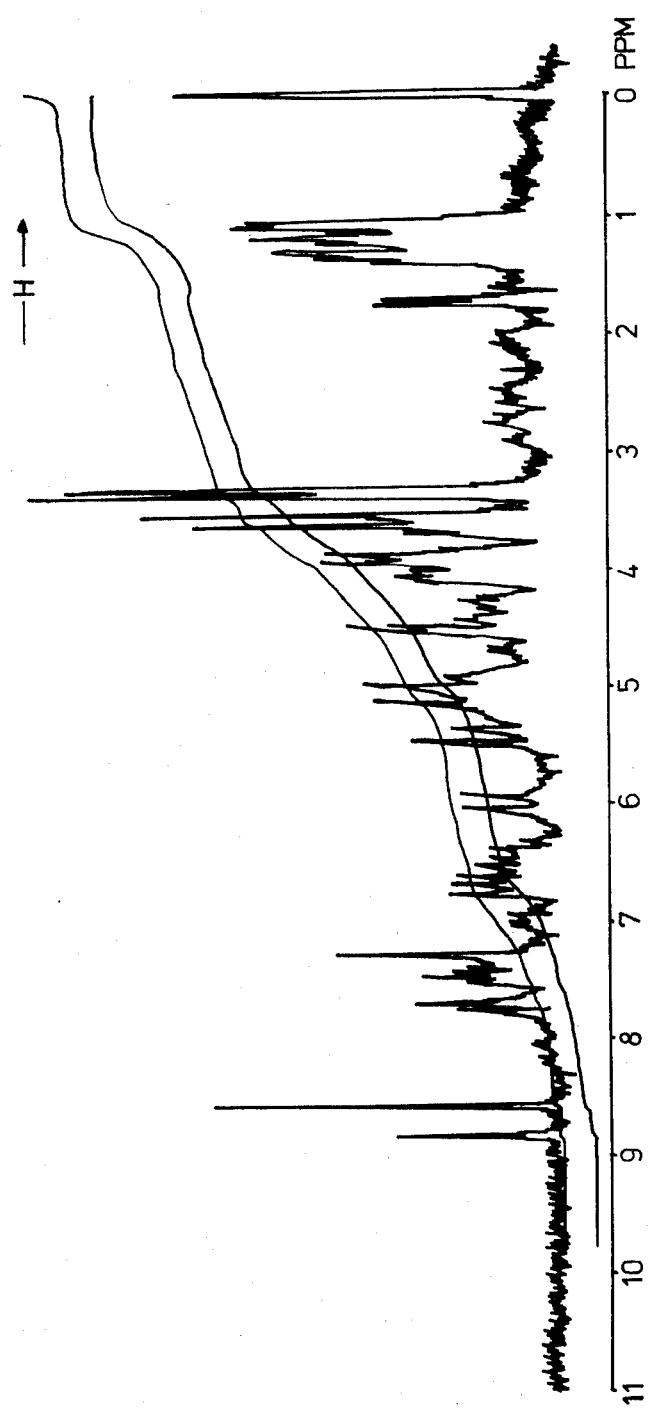

(4) IR absorption spectrum:

The IR absorption spectrum of the antibiotic is shown in FIG. 2 (abscissa: wave number in $cm^{-1}$, ordinate: absorption). When pressed to form KBr tablets, the antibiotic shows absorption bands at the following wavelengths (expressed in reciprocal centimeters):

| Wavelength | Intensity | Wavelength | Intensity |
|---|---|---|---|
| 3450 | s | 1238 | s |
| 2980 | m | 1200 | s |
| 2940 | s | 1120 | s |
| 2900 | m | 1025 | s |
| 1700 | s | 945 | s |
| 1640 | s | 905 | s |
| 1598 | m | 870 | m |
| 1580 | m | 840 | m |
| 1450 | s | 820 | m |
| 1370 | s | 785 | m |
| 1300 | s | | | s = strong,
m = medium (5) $^1H$ nuclear magnetic resonance (NMR) spectrum, given in parts per million (ppm) and vibrations per second (Hz), according to FIG. 3.

Figure 4:
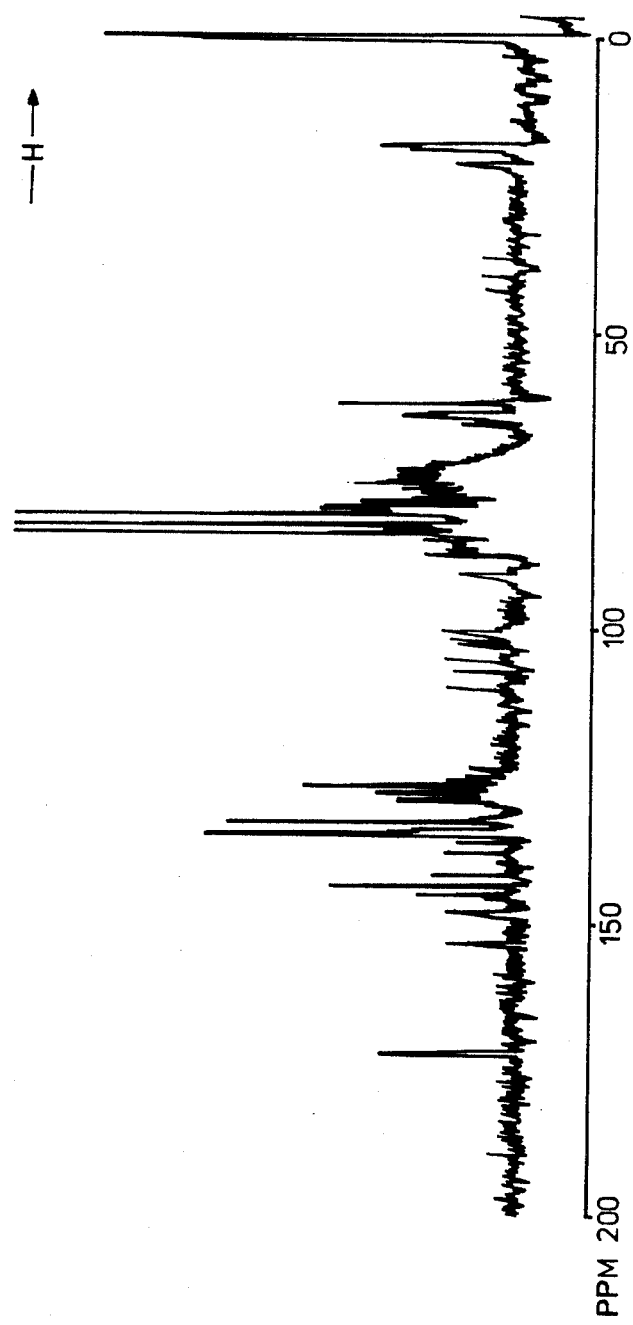

(6) $^{13}C$ NMR spectrum according to FIG. 4

The $^{13}C$ NMR spectrum shows the following signals, given in parts per million (ppm) and vibrations per second (Hz), and their relative intensities:

| Signal No. | Intensity | Signal position, Hz | Signal position, ppm |
|---|---|---|---|
| 1 | 60 | 4214.3 | 167.243 |
| 2 | 28 | 3673.3 | 145.773 |
| 3 | 26 | 3566.9 | 141.550 |
| 4 | 40 | 3473.5 | 137.843 |
| 5 | 81 | 3442.5 | 136.612 |
| 6 | 35 | 3409.2 | 135.293 |
| 7 | 31 | 3320.6 | 131.777 |
| 8 | 28 | 3262.6 | 129.472 |
| 9 | 141 | 3238.3 | 128.511 |
| 10 | 62 | 3231.2 | 128.229 |
| 11 | 51 | 3225.3 | 127.994 |
| 12 | 129 | 3187.2 | 126.481 |
| 13 | 56 | 3052.3 | 121.129 |
| 14 | 65 | 3034.2 | 120.410 |
| 15 | 96 | 3013.0 | 119.568 |
| 16 | 30 | 3002.5 | 119.151 |
| 17 | 30 | 2630.2 | 104.379 |
| 18 | 26 | 2560.4 | 101.606 |
| 19 | 28 | 2515.9 | 99.842 |
| 20 | 26 | 2435.2 | 96.640 |
| 21 | 30 | 2418.1 | 95.961 |
| 22 | 31 | 2397.8 | 95.154 |
| 23 | 26 | 2173.3 | 85.247 |
| 24 | 45 | 2074.4 | 82.322 |
| 25 | 36 | 2062.0 | 81.329 |
| 26 | 33 | 2049.2 | 81.321 |

-continued

| Signal No. | Intensity | Signal position, Hz | Signal position, ppm |
|---|---|---|---|
| 27 | 31 | 2039.8 | 80.974 |
| 28 | 36 | 2031.4 | 80.614 |
| 29 | 46 | 2004.3 | 79.561 |
| 30 | 678 | 1971.1 | 78.222 |
| 31 | 63 | 1955.6 | 77.606 |
| 32 | 836 | 1939.3 | 76.958 |
| 33 | 27 | 1930.6 | 76.617 |
| 34 | 25 | 1927.2 | 76.482 |
| 35 | 29 | 1923.1 | 76.319 |
| 36 | 753 | 1907.6 | 75.703 |
| 37 | 55 | 1898.7 | 75.349 |
| 38 | 91 | 1895.6 | 75.226 |
| 39 | 55 | 1877.9 | 74.523 |
| 40 | 46 | 1848.0 | 73.335 |
| 41 | 47 | 1843.5 | 73.160 |
| 42 | 53 | 1828.1 | 72.549 |
| 43 | 80 | 1812.9 | 71.945 |
| 44 | 37 | 1806.1 | 71.674 |
| 45 | 56 | 1791.1 | 71.079 |
| 46 | 55 | 1777.1 | 70.522 |
| 47 | 46 | 1769.2 | 70.209 |
| 48 | 41 | 1763.9 | 69.998 |
| 49 | 48 | 1745.9 | 69.287 |
| 50 | 38 | 1730.3 | 68.667 |
| 51 | 25 | 1714.1 | 68.023 |
| 52 | 55 | 1564.1 | 62.072 |
| 53 | 43 | 1559.0 | 61.862 |
| 54 | 75 | 1490.2 | 59.140 |
| 55 | 28 | 509.7 | 20.229 |
| 56 | 55 | 457.1 | 18.140 |
| 57 | 67 | 452.7 | 17.965 |
| 58 | 53 | 407.5 | 16.173 |
| 59 | 183 | 0.5 | 0.019 |

In addition, 3 further signals, of low intensity, are visible in FIG. 4, which are not recorded by the data system. They are at 35.74, 38.36 and 40.50 ppm.

(7) The antibiotic is readily soluble in chloroform, acetone, ethyl acetate, acetonitrile, dimethylformamide, dimethylsulphoxide and $C_1$ to $C_6$ alcohols, for example methanol and ethanol; on the other hand, it is sparingly soluble in water, diethyl ether, petroleum ether and cyclohexane.

(8) The antibiotic according to the invention is an amorphous, pale yellow neutral compound which does not migrate on electrophoresis. On vigorous acid hydrolysis, various reducing sugars are split off (for example with 10% by weight aqueous sulphuric acid at 80° C.). As a result, it is easily possible, in the case of thin layer chromatography on a silica gel plate, to render the antibiotic visible with sugar reagents (for example with anisaldehyde-sulphuric acid, thymol-sulphuric acid, vanillin-perchloric acid or dimedone-phosphoric acid) or with phosphomolybdic acid, as a result of characteristic colorations. Some colorations which can be used for the identification are listed in Table 1.

TABLE 1

| No. | Reagent* | Colour | Background |
|---|---|---|---|
| 1 | 10% strength $H_2SO_4$ | brown | white |
| 2 | Iodine | brown | brown-yellow |
| 3 | Phosphomolybdic | blue-green | pale green |
| 4 | Silver nitrate-$NH_3$ | brown | light brown |
| 5 | Thymol-$H_2SO_4$ | red-violet | colourless |
| 6 | Dimedone-$H_3PO_4$ | green (yellow in UV light) | colourless |
| 7 | Anisaldehye-$H_2SO_4$ | green | colourless |
| 8 | Vanillin-$HClO_4$ | brown | colourless |

*The reagents were made up in accordance with the usual prescriptions (compare E. Stahl, Dunnschichtchromatographie, (Thin Layer Chromatography), 2nd edition, Springer Verlag, Berlin, Heidelberg, New York (1967)).

(9) The $R_f$ values of the antibiotic according to the invention on neutral silica gel plates (Messrs. Merck, Darmstadt, West Germany), compared to erythromycin base, in various migrating agents, are shown in Table 2.

TABLE 2

| No. | Migrating agent (parts by volume) | $R_f$ value new antibiotic | $R_f$ value erythromycin base |
|---|---|---|---|
|  | Chloroform + methanol |  |  |
| 1 | 95 + 5 | 0.00 | 0.00 |
| 2 | 90 + 10 | 0.27 | 0.08 |
| 3 | 80 + 20 | 0.59 | 0.21 |
| 4 | 50 + 50 | 0.85 | 0.26 |
| 5 | Chloroform + methanol + ammonia* 40 + 6 + 1 | 0.34 | 0.62 |
| 6 | Methanol | 0.83 | 0.25 |
| 7 | Butanol + glacial acetic acid + water 60 + 20 + 20 | 0.55 | 0.39 |

*aqueous solution containing 25% by weight of ammonia.

The 220 MHz-$^1$H NMR spectrum shown in FIG. 3 was recorded on a solution of the antibiotic in deuterated pyridine, with tetramethylsilane as the internal standard, on an HR-Sc spectrometer from Messrs. Varian Associates, Paolo, Alto, Calif., U.S.A.

The $^{13}$C NMR spectrum (FIG. 4) was measured on a solution of the antibiotic in deuterated chloroform on an XL-100 spectrophotometer (15") of Messrs. Varian at 25.2 MHz, with proton noise decoupling.

(10) The optical votation in methanol (c=0,2446 g/100 ml methanol) $[\alpha]_D^{20}$ is 27,94°±0,52°.

The IR band intensities are designated s, m and w. An s band has at least $\frac{2}{3}$ of the intensity of the strongest band in the spectrum, an m band has an intensity in the range between $\frac{1}{3}$ and $\frac{2}{3}$ of the strongest band and a w band has less than $\frac{1}{3}$ of the intensity of the strongest band. These estimates are made on the basis of the percentage transmission.

The available physio-chemical and spectroscopic data of the antibiotic are in conformity with the following structural formula:

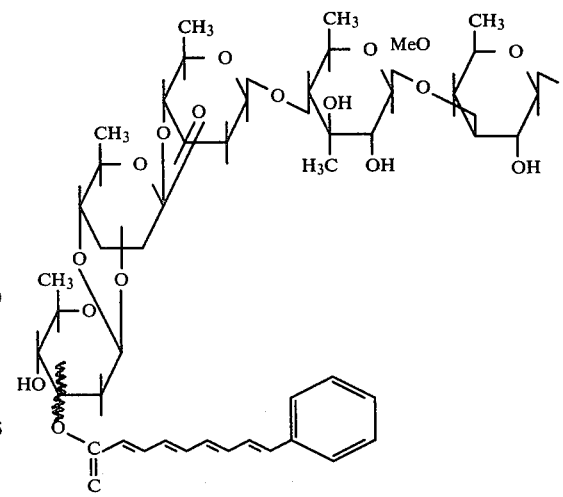

-continued

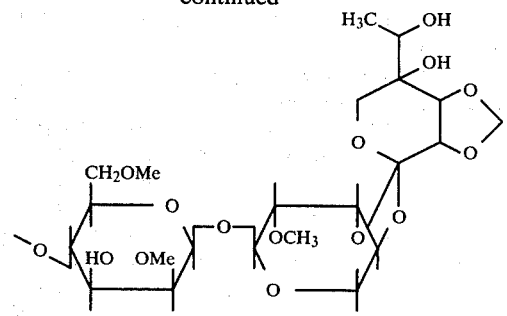

Surprisingly, the antibiotic according to the invention is formed by the above-mentioned spontaneous mutant 34d (Kl;) of the Actinoplanes strain SE-73 and can be isolated in good yield from the culture medium. Further, it is surprising that the antibiotic according to the invention has a powerful antimicrobial, especially antibacterial, action, also against Gram-negative pathogens, without showing the above-mentioned disadvantages of known antibiotics. Additionally, the new antibiotic surprisingly shows the property of promoting growth, and improving feed utilisation, in animals. The present invention therefore represents an advance in pharmacy and technology. The strain Actinoplanes SE-73/34d according to the invention belongs to the class of the Schizomycetes, the order of the Actinoplanes, the family of the Actinoplanaceae and the genus of the Actinoplanes. It has the following characteristics:

The culture characteristics from various nutrient media (observed after 14 days at a growth temperature of 20° to 30° C.) can be seen from the tabulation which follows.

| Czapek agar | G | good to very good |
| --- | --- | --- |
| | SM | orange |
| | SP | pale brownish yellow |
| | Spg. | — |
| CPC | G | good to very good |
| (Casamino-peptone | SM | orange to orange-brown |
| Czapek agar) | SP | brown |
| | Spg. | — |
| Milk agar | G | good to very good |
| | SM | orange |
| | SP | golden brown |
| | Spg. | — |
| | Casein peptonised | |
| Tyrosine agar | G | moderate to good |
| | SM | brown |
| | SP | brown |
| | Spg. | — |
| | Tyrosine crystals not dissolved | |
| Melanin formation | positive | |
| Milk peptonisation | positive | |

G = growth
SM = substrate mycelium
SP = soluble pigment
Spg. = formation of sporangia
— = absence The new Actinoplanes strain carrying the laboratory designation SE-73/34d (Kl.) has been deposited under number ATCC 31,440 at the American Type Culture Collection, 12,301 Parklawn Drive, Rockville, Md. 20,852, U.S.A.

According to the present invention there is further provided a process for the production of a compound according to the present invention in which the Actinoplanes strain SE-73/34d is cultured under aerobic conditions in a nutrient medium containing sources of carbon, nitrogen and mineral and the resulting antibiotic is isolated from the culture broth and/or the mycelium and is purified if necessary.

The process according to the invention can be carried out with the aid of solid, semi-solid or liquid nutrient media. Preferably, aqueous liquid nutrient media are used.

The nutrient media are inoculated in accordance with generally customary methods, for example using slant tubes or flask cultures. The culture is carried out under aerobic conditions and can be effected in accordance with the generally customary methods, for example using shaken cultures in shaking flasks, using air-agitated cultures or using submerged cultures. Preferably, the cultivation is carried out by the aerobic submerged process in aerated fermenters, for example in customary submerged fermentation tanks. It is possible to carry out the culture continuously or discontinuously. Preferably, the discontinuous method is used.

The culturing can be carried out in all nutrient media which are customarily used for cultivating micro-organisms of the order of the Actinomycetales. The nutrient medium must contain one or more assimilable carbon sources and nitrogen sources as well as mineral salts, and these products can be present in the form of defined individual constituents but also in the form of complex mixtures such as are represented, in particular, by biological products of various origins. Suitable carbon sources are all the usual carbon sources. Examples which may be mentioned are starch, molasses, whey powder, dextrin, sugars, such as sucrose, maltose, glucose, lactose, sorbitol and glycerol. Suitable nitrogen sources are all customary organic and inorganic nitrogen sources. Examples which may be mentioned are soya bean flour, cottonseed flour, lentil flour, pea flour, soluble and insoluble vegetable proteins, corn steep liquor, yeast extracts, peptones and meat extract, as well as ammonium salts and nitrates, for example $NH_4Cl$, $(NH)_2SO_4$, $NaNO_3$ and $KNO_3$. The mineral salts, which should be contained in the nutrient medium, for example provide the following ions: $Mg^{++}$, $Na^+$, $K^+$, $Ca^{++}$, $NH_4^+$, $Cl^-$, $SO_4^{--}$, $PO_4^{---}$ and $NO_3^-$, as well as ions of the customary trace elements, such as Cu, Fe, Mn, Mo, Zn, Co and Ni. If the carbon sources or nitrogen sources, or the water used, do not contain these salts or trace elements to a sufficient degree, it is advisable to supplement the nutrient medium accordingly. The composition of the nutrient media can be varied within wide ranges. The nature and composition of the nutrient media will in general advantageously depend on which constituents are particularly advantageously available.

The pH value of the growing cultures should preferable be kept between 6 and 8, especially between 6.5 and 7.5. Too great a drop in pH into the acid region can be avoided by adding an organic or inorganic base, preferably $CaCO_3$. As is customary in fermentation technology, automatic pH regulation can also be effected, in which case sterile organic or inorganic acid, for example $H_2SO_4$, or sterile alkali solution, for example NaOH, is injected at intervals into the culture solution.

It is advisable to ensure that the micro-organisms are brought into adequate contact with oxygen and with the nutrients. This can be effected in accordance with the generally customary methods, such as shaking and stirring.

The culture temperature is preferably between 20° and 40° C., more preferably between 25° and 35° C., and is particularly preferentially about 28° C. The duration of the culture can be varied widely and in this, for example, the composition of the nutrient medium and the culture temperature play a role. The particular optimum conditions can easily be determined by any expert in the microbiological field.

It has been found that the amount of the antibiotic which accumulates in the culture broth in general reaches its maximum 2 to 12, preferably 5 to 8, days after starting the culture.

As is generally the case with microbiological processes, extraneous infections of the culture media should be avoided. To achieve this, the customary precautions are taken, such as sterilisation of the nutrient media, of the culture vessels and of the air required for the aeration. To sterilise the apparatus it is possible to use, for example, steam sterilisation or dry sterilisation.

If, during culturing, an undesirable amount of foam is produced, the customary chemical anti-foam agents can be added, for example liquid fats and oils, oil-water emulsions, paraffins, higher alcohols, such as octadecanol, silicone oils, polyoxyethylene compounds and polyoxypropylene compounds. Foam can also be suppressed or eliminated with the aid of the customary mechanical devices (which, for example, utilise centrifugal forces).

The antibiotic according to the invention can be isolated from the mycelium and/or from the culture medium in accordance with generally customary physicochemical methods. Isolation can for example take place in accordance with the customary extraction processes, precipitation processes and/or chromatography processes. The isolated antibiotic can also be subjected to fine purification with the aid of the methods mentioned. However, for many cases find purification is not necessary, since the impurities which may be present do not adversely influence the activity of the antibiotic. In all isolation operations and purification operations care must be taken that pH values of 7.0 or above, preferably of between 7.0 and 9.0, are maintained. To raise the pH value, inorganic and organic bases can be used, for example ammonia, alkali metal hydroxides and alkaline earth metal hydroxides, alkali metal carbonates and bicarbonates and alkaline earth metal carbonates and bicarbonates, for example KOH, NaOH, $Na_2CO_3$ and $CaCO_3$, trialkylamines, such as triethylamine, or morpholine or pyridine. To find, in the above-mentioned isolation and purification methods, the fractions in which the antibiotic according to the invention is present in the highest concentration or purity, the customary physicochemical methods may be employed, for example measuring the UV band at 365 nm, measuring the $R_f$ values or, preferably, investigating the antimicromial activity. In the present instance, it is particularly advantageous to investigate the activity against *Bacillus subtilis*, for example *Bacillus subtilis* ATCC 6633, by means of the usual plate test (compare, for example, P. Klein, Bakteriologische Grundlagen der chemotherapeutischen Laboratoriumspraxis (Bacteriological Fundamentals of Chemotherapeutic Laboratory Practice), Springer Verlag, Göttingen (1957), page 86 et seq.).

The isolation and purification of the antibiotic according to the invention may, for example where a liquid, aqueous nutrient medium is used, be carried out as follows:

A water-miscible organic solvent is added to the culture broth, including the mycelium, and the batch is thoroughly mixed, whereby, on the one hand, the active compound is extracted from the mycelium whilst, on the other hand, clarification of the culture broth is achieved.

As solvents it is possible to use, for example, lower alkanols, such as methanol, ethanol, n- and i-propanol or t-butanol, dimethylformamide, tetrahydrofurane and, particularly preferentially, acetone. The amount of the solvent can be varied within wide limits. Preferably, about the same volume as that of the culture broth is added. Thereafter, the undissolved constituents (mycelium, precipitated proteins and the like) are separated off by filtration, centrifuging, decanting and the like.

The aqueous-organic solution is advantageously concentrated in vacuo to approximately the volume of the culture medium employed.

If necessary, a pH value above 7.0, for example a pH value of 9.0, is set up by means of a base (compare above), preferably with NaOH. The solution thus obtained will, in the test which follows, be referred to as "Solution 1".

The antibiotic according to the invention can be isolated from "Solution I", and be purified if necessary, by means of customary extraction processes, precipitation processes and/or chromatography processes. The chromatography can be carried out in the form of column chromatography or of preparative thin layer chromatography. As Adsorbents it is possible to employ all the customary (non-acidic) inorganic or organic adsorbents, such as, for example, aluminium oxide, silica gel, magnesium silicate, active charcoal, cellulose, cellulose derivatives, synthetic resins, such as polyamides, polyamide derivatives and the like, for example acetylated polyamide, or dextran gels. A great diversity of solvents or solvent mixtures, in which the antibiotic according to the invention is soluble can be used as migrating agents in the preparative thin layer chromatography. Preferably, a mixture of chloroform and methanol (for example 9:1 parts by volume) is employed. As migrating agents for column chromatography it is again possible to use solvents or solvent mixtures in which the antibiotic according to the invention is soluble. Examples which may be mentioned are carbon tetrachloride, methylene chloride and, preferably, chloroform.

Preferably, extraction processes, optionally combined with chromatography processes and precipitation processes, are used to isolate the antibiotic according to the invention. In carrying out the extraction steps, care must be taken that depending on whether the antibiotic according to the invention is to be present in the aqueous or organic phase, the extractants are selected so that the antibiotic is, respectively, sparingly soluble or readily soluble therein.

The extraction process can, for example, be carried out as follows:

"Solution I" is extracted with water-immiscible, organic solvents in accordance with customary methods (shaking, counter-current processes and the like). Solvents which can be used are the customary extractants, for example esters, such as ethyl acetate and butyl acetate, higher alcohols, such as amyl alcohols, for example n-amyl alcohol, water-immiscible ketones, for example methyl isobutyl ketone, and chlorinated lower hydrocarbons, for example chloroform or methylene chloride. Preferably, ethyl acetate and butyl acetate, especially ethyl acetate, are used.

If ethyl acetate (and/or butyl acetate) is employed for extracting the "Solution I", the aqueous phase is discarded, since the antibiotic according to the invention is present in the organic phase.

The organic phase is concentrated, for example to about 1/10 to 1/30 of the original volume. The antibiotic according to the invention is then precipitated in accordance with the customary methods by adding an organic precipitant (solvent), in which the antibiotic according to the invention is sparingly soluble, for example diethyl ether or saturated straight-chain, branched or cyclic hydrocarbons, for example petroleum ethers, n-hexane or cyclohexane.

The crude antibiotic can be subjected to fine purification either by liquid-liquid distribution (for example according to the Craig method) or, if desired, according to the customary chromatographic methods (column chromatography or preparative thin layer chromatography), for which the adsorbents which can be used are, as already mentioned, the customary non-acidic inorganic and organic adsorbents, for example aluminium oxide, silica gel, magnesium silicate, active charcoal, cellulose, cellulose derivatives, synthetic resin, such as polyamides and polyamide derivatives, for example acetylated polyamide, dextran gels, ion exchangers and the like.

If, instead of ethyl acetate or butyl acetate, another solvent, for example n-butanol, is used in the extraction of the "Solution I", the aqueous phase is discarded, since the antibiotic according to the invention is predominantly present in the organic phase. In that case, the organic solvent is preferably concentrated to about 1/10 to 1/30 of the original volume and precipitation is effected in accordance with the customary methods by adding a suitable organic precipitant, in which the antibiotic according to the invention is surprisingly soluble, for example diethyl ether or saturated straight-chain or branched or cyclic hydrocarbons, for example petroleum ether, n-hexane or cyclohexane. The precipitate is dissolved in water and the solution is freeze-dried. The resulting crude product can be concentrated, if appropriate by extraction with ethyl acetate or butyl acetate, wherein undesired concomitant materials are very lagely insoluble, and can be purified in accordance with the customary chromatographic methods, for example by column chromatography, perparative thin layer chromatography with the aid of the customary adsorbents (compare also the above comments) or liquid-liquid distribution. For purification it is also possible, as already mentioned above, to precipitate the antibiotic according to the invention from a solution of the crude product in an organic solvent (for example chloroform and methylene chloride) by means of a suitable organic precipitant in which the antibiotic according to the invention is sparingly soluble, for example diethyl ether or saturated straight-chain or branched or cyclic hydrocarbons, for example petroleum ether, n-hexane and cyclohexane.

The antibiotic can be obtained from its solutions in accordance with the customary methods, for example by evaporating the solvent, freeze-drying and the like.

The active compound according to the invention displays a powerful antimicrobial activity, coupled with low toxicity. These properties enable it to be used as a chemotherapeutic active compound in medicine and as a substance for preserving inorganic and organic materials, especially organic materials of all kinds, for example polymers, lubricants, paints, fibres, leather, paper and timber, and foodstuffs and water.

The active compound according to the invention is active against a very broad spectrum of micro-organisms. With its aid it is possible to combat Gram-negative and Gram-positive bacteria and bacteria-like micro-organisms.

The active compound according to the invention is particularly active against bacteria and bacteria-like micro-organisms. It is therefore particularly suitable, in medicine, for the prophylaxis and chemotherapy of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus, Staph. epidermis* and *Staph. aerogenes* and *Gaffkya tetragena* (Staph.=Staphylococcus); Lactobacteriaceae, such as Streptococci, for example *Streptococcus pyogenes*, α- and β-haemolysing Streptococci, non-(γ)-haemolysing Streptococci, *Str. viridans, Str. faecalis* (Enterococci), *Str. alalactiae, Str. lactis, Str. equi* and *Str. anaerobis,* and *Diplococcus pheumoniae* (Pneumococci) (Str.=Streptococcus); Neisseriaceae, such as Neisseriae, for example *Neisseria gonorrhoeae* (Gonococci), *N. meningitidis* (Meningococci), *N. catarrhalis* and *N. flava* (N=Neisseria); Corynebacteriaceae, such as Corynebacteria, for example *Corynebacterium diphtheriae, C. pyogenes, C. diphtheroides, C. acnes, C. parvum, C. bovis, C. renale, C. ovis* and *C. murisepticum,* Listeria bacteria, for example *Listeria monocytogenes,* Erysipelothrix bacteria, for example *Erysipelothrix insidiosa* and Kurthia bacteria, for example *Kurthia zopfii* (C.=Corynebacterium); Mycobacteriaceae, such as pathogens of mycobacterioses, for example *Mycobacterium tuberculosis, M. bovis, M. avium,* and so-called atypical mycobacteria of the Runyon groups I, II, III and IV, and *M. leprae* (M.=Mycobacterium); Enterobacteriaceae, such as Escherichiae bacteria of the coli group; Escherichia bacteria, for example *Escherichia coli,* Enterobacter bacteria, for example *E. aerogenes* and *E. cloacae,* Klebsiella bacteria, for example *K. pneumoniae* and *K. ozaenae,* Erwiniae, for example Erwinia spec., Serratia, for example *Serratia marcescens* (E.=Enterobacter) (K.=Klebsiella), Proteae bacteria of the Proteus group: Proteus, for example *Proteus vulgaris, Pr. morganii, Pr. rettgeri* and *Pr. mirabilis,* Providencia, for example Providencia sp. (Pr.=Proteus), Salmonelleae: Salmonella bacteria, for example *Salmonella paratyphi* A and B, *S. typhi, S. enteritidis, S. Chloerae suis* and *S. syphimurium* (S.=Salmonella), and Shigella bacteria, for example *Shigella dysenteriae, Sh. ambigua, Sh. flexneri, Sh. boydii* and *Sh. sonnei* (Sh.=Shigella); Spirillaceae, such as Vibrio bacteria, for example Vibrio chloreae, V. proteus and *V. fetus* (V.=Vibrio), and Spirillum bacteria, for example *Spirilum minus;* Bacillaceae, such as aerobic spore-forming organisms, for example *Bacillus anthracis* (*B. subtilis* and *B. cereus*) (B.=Bacillus) and anaerobic spore-forming organisms—Clostridia, for example *Clostridium perfringens, Cl. septicum, Cl. oedematiens, Cl. histolyticum, Cl. tetani* and *Cl. botulinum* (Cl.=Clostrodium); Mycoplasma, such as, for example, *Mycoplasma pneumoniae, M. hominis, M. suis pneumoniae, M. gallisepticum* and *M. hyorhinis* (M.=Mycoplasma).

The above list of pathogens is purely illustrative and is in no way to be interpreted as restrictive.

The following may be mentioned as examples of illnesses which can be prevented, alleviated and/or cured by the active compound according to the invention; illnesses of the respiratory passages and of the pharyngeal cavity; otitis, pharyngitis, pneumonia, peritonitis, pyelonephritis, cystitis, endocarditis, systemic infections, bronchitis, arthritis, local inflammations and skin infections.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alchol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 to 25 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitibeally, subcutaneously and intravenously), rectally or locally, preferably orally or parenterally, especially intramuscularly or intravenously, and if appropriate also by a continuous intravenous drip. Preferred pharmaceutical compositions and medicaments are therefore those adapted for administration such as oral or parenteral administration. Administration in the method of the invention is preferably oral or parenteral administration.

In general it has proved advantageous to administer orally or parenterally amounts of from 10 mg to 1,000 mg/kg preferably 50 mg to 500 mg/kg, of body weight per day, optionally in the form of several individual administrations, to achieve effective results. An individual administration preferably contains 15 mg to 150 mg/kg, especially 10 mg to 100 mg/kg, of body weight. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, whilst other cases the upper limit mentioned must be exceeded to achieve the desired results. Where larger amounts are administered it can be advisable to divide these into several individual administrations over the course of the day.

The active compound according to the invention can also be used in all areas of animal breeding and animal husbandry as agents for improving (by promoting and accelerating) the growth and for improving the feed utilization of healthy and sick animals.

The activity of the active compound according to the invention is largely independent of the species and sex of the animals. The active compound according to the invention proves particularly valuable in the rearing and keeping of young animals and fattening animals.

The following stock animals and pets may be mentioned as examples of animals for which the active compound according to the invention can be used for promoting and accelerating growth and for improving feed utilisation: warm-blooded animals, such as cattle, pigs, horses, sheep, goats, cats, dogs, rabbits, fur-bearing animals, for example mink and chinchillas, poultry, for example chicken, geese, ducks and turkeys, pigeons, parrots and canaries, and cold-blooded animals, such as fish, for example carp, and reptiles, for example snakes.

The amount of the active compound according to the invention which is administered to the animals to achieve the desired effect can be varied substantially, because of the favourable properties of the active compound. It is preferably 5 to 500, in particular 10 to 100, mg/kg of body weight daily. The period of administration can be from a few hours or days up to several years. The appropriate amount of active compound and the appropriate period of administration depend, in particular, on the species, age, sex, state of health and nature of keeping of the animals, and can easily be determined by any expert.

The active compound according to the invention is administered to the animals by the customary methods. The nature of the administration depends, in particular, on the species, the behaviour and the state of health of the animals. Thus, administration can be effected orally or parenterally, once or several times daily at regular or irregular intervals. For reasons of expediency, in most cases oral administration, in particular in the rhythm of the intake of food and/or drink by the animals, is to be preferred.

The active compound according to the invention can be administered as the pure substance or in the formulated form, that is to say mixed with non toxic inert carriers of any type, for example with carriers and in formulations such as are described above in the case of the pharmaceutical formulations.

The active compound according to the invention, optionally in the formulated form, can also be administered in a suitable form together with pharmaceutical active compounds mineral salts, trace elements, vitamins, proteins, fats, colorants, and/or flavouring agents.

Oral administration together with the feed and/or drinking water is recommended, the active compounds being added to the total amount or only portions of the feed and/or drinking water as required.

The active compound according to the invention can be admixed to the feed and/or drinking water in accordance with customary methods by simple mixing as the pure substance, preferably in the finely divided form, or in the formulated form mixed with edible non-toxic carriers, and optionally also in the form of a premix or a feed concentrate.

The feed and/or drinking water can contain the active compound according to the invention in a concentration of, for example, about 5 to 500 ppm, in particular 10 to 100 ppm (weight). The optimum level of the concentration of the active compound in the feed and/or drinking water depends, in particular, on the amount of feed and/or drinking water taken in by the animals and can easily be determined.

The present invention thus further relates to a medicated feed comprising a compound of the present invention and a nutritious material.

The nature of the feed and its composition is irrelevant. All the customary, commercially available or specific feed compositions, which preferably contain the customary equilibrium of energy substances and builder substances, including vitamins and mineral substances, necessary for balanced nutrition can be used. The feed can be composed for example, of vegetable substances, for example hay, beet, cereals and cereal by-products, animal substances, for example meat, fats and bonemeal, fish products, vitamins, for example vitamin A, D complex and B complex, proteins, aminoacids, for example DL-methionine, and inorganic substances, for example lime and sodium chloride.

Feed concentrate contain the active compound according to the invention alongside edible substances, for example rye flour, maize flour, soya bean flour or lime, optionally with further nutrients and builder substances, as well as proteins, mineral salts and vitamins. They can be prepared by the customary mixing methods.

In premixes and feed concentrates, preferably, the active compound can optionally also be protected from air, light and/or moisture by suitable agents which coat its surface, for example with non-toxic waxes or gelatine.

The following is an example of the composition of a feed for rearing chicks, which contains the active compound according to the invention: 200 g of wheat, 340 g of maize, 361 g of coarse soya bean meal, 60 g of beef tallow, 15 g of dicalcium phosphate, 10 g of calcium carbonate, 4 g of iodinated sodium chloride, 7.5 g of a vitamin/mineral mixture and 2.5 g of an active compound premix give, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridozine, 20 meg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains the active compound according to the invention in the desired amount, for example 100 mg, and also 1 g of DL-methionine as well as an amount of soya bean flour such that 2.5 g of premix are formed.

The following is an example of the composition of a feed for rearing pigs, which contains the active compound according to the invention: 630 g of shredded cereal feed (composed of 200 g of maize, 150 g of shredded barley, 150 g of shredded oats and 130 g of shredded wheat), 80 g of fish meal, 60 g of coarse soya bean meal, 60 g of tapioca meal, 38 g of brewers' yeast, 50 g of a vitamin/mineral mixture for pigs (composition, for example, as for the chick feed), 30 g of linseed cake meal, 30 g of maize gluten feed, 10 g of soya bean oil, 10 g of sugar cane molasses and 2 g of an active compound premix (composition, for example, as for the chick feed) give, after careful mixing, 1 kg of feed.

The feed mixtures indicated are intended preferably for rearing and fattening chicks or pigs respectively, but they can also be used, in the same or a similar composition, for rearing and fattening other animals.

The good antimicrobial activity of the antibiotic according to the invention can be demonstrated by the following experiments:

(a) In vitro experiments:

The antibiotic according to the invention is diluted with Müler-Hinton nutrient broth to a content of 200 μg/ml, 1% of glucose being added. The nutrient solution in each case contains $1 \times 10^5$ to $2 \times 10^5$ bacteria per milliliter. The test tubes containing this batch are in each case incubated for 18 hours and the degree of turbidity is then determined. Freedom from turbidity indicates an effect. At a dosage of 200 μg/ml, the following bacterial cultures are free from turbidity: *Escherichia coli* 14; *Escherichia coli* C 165; *Proteus vulgaris* 1017; Klebsiella K 10; Klebsiella 63; Salmonella sp; Shigella sp.; Enterobacter sp.; Serratia sp.; Proteus, indole-negative, sp.; Proteus, indole-positive, sp.; *Pasteurella pseudotuberculosis; Staphylococcus aureus* 133; Neisseria catarrhalis sp.; *Diplococcus pheumoniae* sp.; *Streptococcus pyogenes* W; Enterococcus sp.; Lactobacillus sp.; *Coryne-bacterium diphtheriae gravis; Corynebacterium pyogenes* M; *Clostridium botulinum; Clostridium tetani; Pseudomonas aeruginosa* sp.; *Aeromonas hydrophila* sp.; Mycoplasma sp. (Sp. = "species" = strains which have not been identified in more detail but are characteristic).

(b) In vivo experiments:

Table 1 which follows shows the effect of the antibiotic according to the invention against a range of bacteria in animal experiments with white mice. The white mice of strain $CF_1$ are infected intraperitoneally with the particular bacterial species mentioned.

TABLE 1

Animal experiment with white mice
Determination of the $ED_{50}$ after 24 hours

| Germ | Dose in mg of the antibiotic according to the invention per kg of body weight |
|---|---|
| *Escherichia coli* 165 | 2 × 600 |
| *Staphylococcus aureus* | 1 × 400 |

| | |
|---|---|
| Therapy: One administration: | 30 minutes after infection, subcutaneous |
| Two administration: | 30 minutes after and 90 minutes after infection. |

The $ED_{50}$ is the dose at which 50% of the infected animals still survive after 24 hours.

The good activity of the antibiotic according to the invention as a means of promoting the growth of animals can be demonstrated by the following experiment:

In feeding experiments, the substance is mixed with the feed and fed to chicks (given feed ad libitum). The dose is 10 or 20 ppm. Comparison is made against a negative control (feed without additives). Duration of the experiment: 14 days.

| Experiment Group | Increase in weight in % | Feed consumption in % | Feed utilisation in % |
|---|---|---|---|
| Control | 100 | 100 | 100 |
| Antibiotic according to the invention | | | |
| 10ppm | 102.8 | 102.8 | 100 |
| 20ppm | 103.5 | 102.3 | 98.5 |

The following Examples 1 to 3 illustrate the production of the antibiotic according to the present invention and Examples 4 to 6 illustrate the purification of the antibiotic thereby obtained.

EXAMPLE 1

A mycelium, grown on slant agar of the following composition (percentages by weight)

| | |
|---|---|
| Peptone | 0.25% |
| Casein hydrolysate, acidic | 0.25% |

-continued

| | |
|---|---|
| K₂HPO₄ . 3H₂O, analytical grade | 0.1% |
| KCl, analytical grade | 0.05% |
| MgSO₄, analytical grade | 0.05% |
| FeSO₄, analytical grade | 0.01% |
| Cane sugar | 3.0% |
| Agar | 2.0% |
| Water | to make up to 100% | of the strain Actinoplanes SE-73/34d (Kl.) is trans inoculated, to prepare the preculture, onto 140 ml portions, contained in a liter Erlenmeyer flasks, of a sterile nutrient solution (referred to in the text which follows as nutrient solution A) of the following composition (percentages by weight)

| | |
|---|---|
| Soya flour, defatted | 3.0% |
| Glycerol, pure | 3.0% |
| CaCO₃, analytical grade | 0.2% |
| Water | to make up to 100% | additionally containing a neutral polyol which contains hydroxyl groups (1 drop of polyol per 140 ml of nutrient solution, as an anti-foam agent).

After culturing the strain for four days on a rotary shaking machine at 28° C., 1 ml of portions of the shaken culture thus produced are trans-inoculated onto 140 ml portions, contained in 1 liter Erlenmeyer flasks, of a sterile nutrient solution (referred to as "nutrient solution 15" in the text which follows) having the following composition (percentages by weight)

| | |
|---|---|
| Soya flour, defatted | 0.0% |
| Glycerol, pure | 2.0% |
| Glucose, pure | 1.0% |
| CaCO₃, analytical grade | 0.2% |
| Water | to make up to 100% | additionally containing a neutral polyol which contains hydroxyl groups (1 drop of polyol per 140 ml of nutrient solution, as an anti-foam agent).

After culturing the strain for 5 days on a rotary shaking machine at 28° C., samples of the cultures are centrifuged. The clear, supernatant solution is tested, in the agar plate hole test against *Bacillus subtilis* ATCC 6633. The antibiotic according to the invention, present in the culture solution, produces growth inhibition zones of about 18 mm diameter. The antibiotic according to the invention is isolated from the culture broths as described in Example 3.

EXAMPLE 2

8 liter batches of nutrient solution of the following composition (percentages by weight)

| | |
|---|---|
| Soya flour, defatted | 2.0% |
| Glycerol | 2.0% |
| Dextrin | 1.0% |
| CaCO₃ | 0.2% |
| Water | to make up to 100% | also containing 2 ml of anti-foam agent are introduced into a glass fermenter equipped with a stirrer and aerating device, brought to pH 7.0 with sodium hydroxide solution and sterilised at 120° C. After the solution has cooled, the fermenters are each inoculated with 140 ml of a shaken culture of Actinoplanaceae strain SE-73/34d (Kl.) which had been grown in "nutrient solution A" for 4 days, and are aerated with about 2 liters of air per minute at about 150 revolutions of the stirrer per minute, and kept at a temperature of 28° C. 18 hours after starting the culture, the revolutions of the stirrer are increased to 300 revolutions per minute. After 90 hours, the culture is terminated.

A sample of the culture broth is mixed with an equal volume of acetone and the mixture is shaken vigorously and centrifuged after 30 minutes. The antibiotic formed in the culture is determined in the supernatant solution by high pressure liquid chromatography, in the following manner:

| | |
|---|---|
| Apparatus: | Knauer |
| Column: | Steel column, length 25 cm, internal diameter, 4 mm |
| Mobile phase: | Methanol/water 80:20 (V/V) |
| Stationary phase: | C₈, 7.5μ |
| Pressure: | 180 bar |
| Flow rate: | 1.5 ml/minute |
| Detection: | λ = 365 nm |
| Amount charged in: | 125 μl of an 0.1 or 0.01% strength solution |
| Charging system: | Sample loop |

The culture broth contains 228 mg/l of active compound.

The preparative purification of the antibiotic according to the invention by means of high pressure liquid chromatography is carried out analogously to the above-mentioned analytical determination, with the following conditions being changed:

| | |
|---|---|
| Pressure: | 75 bar |
| Flow rate: | 4 ml/minute |
| Detection: | λ = 308 nm, λ = 365 nm |
| Amount charged in: | 10 mg/50 μl system |

From 300 mg of material employed, 102 mg of pure antibiotic are obtained.

EXAMPLE 3

The culture broths, obtained according to Example 2, from 5 glass fermenters (5×8 liters) are combined, 48 liters of acetone are added, and the mixture is stirred for one hour at about 25° C. and then centrifuged. The clear supernatant liquor, freed from the extracted mycelium, is concentrated in vacuo at 20° to 35° C. to about 35 liters, brought to pH 6.5 with sodium hydroxide solution and extracted with 18 liters of ethyl acetate.

The organic phase is dried with 500 g of sodium sulphate, evaporated to about 1 liter in vacuo and mixed with 2 liters of cyclohexane.

After filtering off the precipitate which has separated out, and drying it in air, 8 g of the crude antibiotic according to the invention are obtained.

EXAMPLE 4

Purification of the antibiotic according to the invention by preparative thin layer chromatography (TLC).

In the thin layer chromatogram of the crude antibiotic obtained according to Example 3, the antibiotic according to the invention is present in the main zone, with an R$_f$ value of 0.34. (Mobile phase No.5 from Table 2, silica gel plates, Messrs. Merck, Darmstadt, West Germany, silica gel 60 F₂₅₄). 1.00 g of the crude antibiotic are separated (using the mobile phase No.5 from Table 2) on 20 silica gel plates (20×20 cm) (silica gel PSC F$_{254}$, Messrs. Merck).

The main zone, having an R$_f$ value of 0.34, is isolated. Yield: 327 mg.

EXAMPLE 5

Purification of the antibiotic according to the invention by column chromatography.

3.5 g of the crude antibiotic obtained according to Example 3 are chromatographed, in mobile phase No.5 from Table 2, on a 100 cm long column of 5 cm diameter, filled with neutral silica gel (silica gel 60, particle size less than 0.063, Messrs. Merck, Darmstadt).

The main fraction, absorbing at 365 nm, is collected. The eluate is evaporated in vacuo and the residue is reprecipitated from ethyl acetate/petroleum ether. The antibiotic is dried at 100° C. for 4 days in a high vacuum at 0.01 mm Hg.

Yield: 1.8 g.

EXAMPLE 6

Purification by Craig distribution 50 g of a crude product prepared according to the process described in Example 3 are subjected to a Craig distribution, using an apparatus from Messrs. Labortec F. Schmidiger, Basel (Switzerland), with 250 cm$^3$ phase volume and a solvent mixture of petroleum ether, ethyl acetate, dimethylformamide and water in the ration of 1.5:8.5:5.5 (by volume).

180 distribution steps are carried out, and after 60 steps the upper phase is fractionallt withdrawn. The antibiotic is present in fractions 21–68. The upper phase collected is washed with water, largely evaporated in vacuo and mixed with 100 ml of ethyl acetate. The antibiotic is precipitated by adding 1 liter of diethyl ether. It is filtered off and dried in a high vacuum at 100° C. and 0.01 mm Hg for 4 days.

Yield: 17.0 g

The plate diffusion test mentioned in the examples is carried out as follows (compare P. Klein, Bakteriologische Grundlagen der Chemotherapeutischen Laboratoriumspraxis (Bacteriological Fundamentals of Chemotherapeutic Laboratory Practice), Springer-Verlag, Göttingen (1957), pages 86 et seq.):

Holes are punched in an agar plate infected with *Bacillus subtilis* ATCC 6633. The material to be tested is introduced, as an aqueous solution, into these holes. The plate is then incubated for about 16 hours at 37° C. Inhibition areolae indicate activity against the germ used. Conclusions as to the content of antibiotic according to the invention can be drawn from the size of the inhibition areolae.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound, but which nonetheless, upon administration to a warm-blooded animal is converted in the patient's body to the active compound.

What is claimed is:

1. A compound which is an antibiotic of the formula

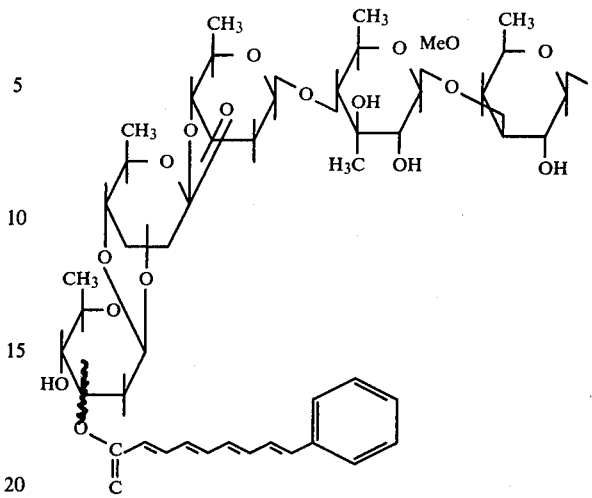

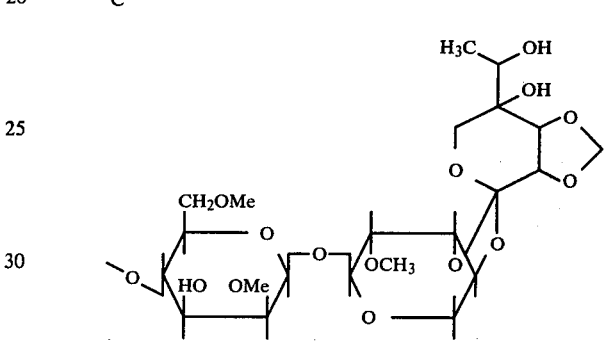

2. A process for the preparation of a compound as claimed in claim 1 in which the Actinoplanes strain SE 73/34d, ATCC 31440 is cultured under aerobic conditions in a nutrient medium containing sources of carbon, nitrogen and mineral substances until substantial antibiotic activity is imparted to said medium and the resulting antibiotic is isolated from the culture broth and/or the mycelium.

3. A process according to claim 2, in which the culture temperature is between 20° C. and 40° C.

4. A process according to claim 2 or 3, in which the pH value of the growing culture is pH 6 to pH 8.

5. A pharmaceutical composition containing as an active ingredient an antibacterially effective amount of a compound according to claim 1 in admixture with a solid or liquefied diluent.

6. A pharmaceutical composition of claim 5 in the form of a sterile or physiologically isotonic aqueous solution.

7. A composition according to claim 5 containing from 0.5 to 95% by weight of the said active ingredient.

8. A medicament in dosage unit form comprising an antibacterially effective amount of a compound according to claim 1 together with an inert pharmaceutical carrier.

9. A medicament of claim 8 in the form of tablets, pills, dragees, capsules, ampoules or suppositories.

10. A method of combating bacterial diseases in warm-blooded animals which comprises administering to the animals an antibacterially effective amount of an active compound of claim 1 either alone or in admixture with a diluent or in the form of a medicament.

11. A method according to claim 9 in which the active compound is administered orally or parenterally in an amount of 50 to 500 mg per kg body weight per day.

12. A medicated fodder comprising an amount of a compound of claim 1 effective for improving the growth and feed utilization of animals together with a nutritious material.

13. A medicated fodder of claim 12 wherein the nutritious material is an animal food or drinking water.

14. A medicated fodder of claim 12 in the form of a concentrate.

15. A medicated fodder of claim 12 in the form of a premix.

* * * * *

UNITED STATES PATENT AND TRADEMARK OFFICE
CERTIFICATE OF CORRECTION

PATENT NO. : 4,264,591
DATED : Apr. 28, 1981
INVENTOR(S) : Klaus Bauer

It is certified that error appears in the above-identified patent and that said Letters Patent are hereby corrected as shown below:

Title Page, Priority, Delete "Oct. 18," and insert --Nov. 10,--.

Signed and Sealed this

Twenty-second Day of September 1981

[SEAL]

Attest:

GERALD J. MOSSINGHOFF

Attesting Officer

Commissioner of Patents and Trademarks